United States Patent
Dewan et al.

(10) Patent No.: US 10,881,382 B2
(45) Date of Patent: Jan. 5, 2021

(54) METHOD AND SYSTEM FOR DETERMINING QUALITY OF SEMEN SAMPLE

(71) Applicant: SIGTUPLE TECHNOLOGIES PRIVATE LIMITED, Bangalore (IN)

(72) Inventors: Karan Dewan, Bangalore (IN); Bharath Cheluvaraju, Bangalore (IN); Tathagato Rai Dastidar, Bangalore (IN); Apurv Anand, Bangalore (IN); Rohit Kumar Pandey, Bangalore (IN)

(73) Assignee: Sigtuple Technologies Private Limited, Bangalore (IN)

( * ) Notice: Subject to any disclaimer, the term of this patent is extended or adjusted under 35 U.S.C. 154(b) by 0 days.

(21) Appl. No.: 15/753,235

(22) PCT Filed: Dec. 7, 2017

(86) PCT No.: PCT/IB2017/057715
§ 371 (c)(1),
(2) Date: Feb. 16, 2018

(87) PCT Pub. No.: WO2018/104897
PCT Pub. Date: Jun. 14, 2018

(65) Prior Publication Data
US 2020/0205790 A1 Jul. 2, 2020

(30) Foreign Application Priority Data
Dec. 8, 2016 (IN) .............................. 201641042035

(51) Int. Cl.
*A61B 1/005* (2006.01)
*G01N 21/01* (2006.01)
(Continued)

(52) U.S. Cl.
CPC .......... *A61B 10/0058* (2013.01); *G01N 1/30* (2013.01); *G01N 21/01* (2013.01); *G01N 33/49* (2013.01);
(Continued)

(58) Field of Classification Search
None
See application file for complete search history.

(56) References Cited

U.S. PATENT DOCUMENTS 9,495,764 B1 * 11/2016 Boardman ......... G06K 9/00201
2004/0146848 A1 7/2004 Kislev et al.
(Continued)

FOREIGN PATENT DOCUMENTS

| EP | 2 781 945 | 9/2014 |
| IN | 264556 | 1/2015 |
| JP | 5092149 | 12/2009 |

OTHER PUBLICATIONS

Non-Final Office Action for U.S. Appl. No. 15/753,219, dated May 1, 2020.
(Continued)

*Primary Examiner* — Gautam Prakash
*Assistant Examiner* — Lydia Edwards
(74) *Attorney, Agent, or Firm* — Foley & Lardner LLP

(57) ABSTRACT

Disclosed herein is method and system for determining quality of semen sample. Trajectories of objects, identified in each of plurality of image frames of semen sample, are generated by tracking movement of the objects across image frames, and compensating a drift velocity of the semen sample. Further, generated trajectories are classified into sperm and non-sperm trajectories. Finally, total concentration estimate and total motility estimate of the semen sample are computed to generate a semen quality index, which indicates quality of the semen sample. In an embodiment, (Continued)

the method of present disclosure uses a multi-level Convolutional Neural Network (CNN) analysis technique for effectively classifying the object trajectories into sperm and non-sperm objects. Also, since the present method includes estimating and compensating drift velocity in the semen sample, it enhances overall accuracy of motility estimation and semen quality analysis.

20 Claims, 9 Drawing Sheets

(51) Int. Cl.
*G01N 33/50* (2006.01)
*A61B 10/00* (2006.01)
*G01N 1/30* (2006.01)
*G01N 33/49* (2006.01)
*G02B 21/34* (2006.01)

(52) U.S. Cl.
CPC ..... *G01N 33/5026* (2013.01); *G01N 33/5029* (2013.01); *G02B 21/34* (2013.01); *G01N 2021/0118* (2013.01)

(56) References Cited

U.S. PATENT DOCUMENTS

2007/0298454 A1\* 12/2007 Green ................. G06T 7/0012
 435/34
2014/0248656 A1 9/2014 Demirci et al.
2015/0024385 A1 1/2015 Parrish

OTHER PUBLICATIONS

International Search Report from PCT Application No. PCT/IB2017/057379, dated Feb. 5, 2018, pp. 1-2.
International Search Report from PCT Application No. PCT/IB2017/057715, dated Feb. 16, 2018, pp. 1-4.
Written Opinion from PCT Application No. PCT/IB2017/057379, dated Feb. 5, 2018, pp. 1-5.
Written Opinion from PCT Application No. PCT/IB2017/057715, dated Feb. 16, 2018, pp. 1-6.

\* cited by examiner

METHOD AND SYSTEM FOR DETERMINING QUALITY OF SEMEN SAMPLE

CROSS-REFERENCE TO RELATED APPLICATIONS

The present application is a National Stage of PCT Application No. PCT/IM2017/057715, filed Dec. 7, 2017, which claims priority to Indian Patent Application No. 201641042035, filed Dec. 8, 2016, The contents of both applications are incorporated herein by reference in their entirety.

TECHNICAL FIELD

The present subject matter is related, in general, to physiological analysis of biological samples, and more particularly, but not exclusively, to a method and system for determining quality of semen sample.

BACKGROUND

Semen quality assessment is performed for multiple reasons, ranging from analysis of male fertility to results of vasectomy. Generally, the assessment is performed manually by experts who view the live sperm sample under a microscope, and obtain parameters such as sperm concentration per unit volume, morphological quality of the sperms, motility of the sperms, and the presence of non-sperm objects in the semen, for example white blood cells, crystals, spermatogonium cells, and the like. Based on the above criteria, which are measured along specific scales, the decision about the quality of semen is made.

Currently, the number of requests for conducting the semen quality analysis tests have been remarkably increasing. To estimate the sperm concentration and motility, an expert typically manually counts the number of sperms visible in a field of view of a microscope. Also, special counting chambers such as Maklar chamber, or its variants can be used for counting purpose. However, the manual process of counting is subjective, and may not be repeatable for a given semen sample. Thus, manual counts from different experts vary significantly.

Some of the automated quality analysis systems, such as Computer Aided Semen Analyzer (CASA) systems, aim to partially automate this process, but have limited accuracy. Other analysis systems, which do not involve use of microscopic analysis exhibit improved accuracy. However, most of these systems have a high cost, which make them unsuitable for use in most laboratories in developing countries.

SUMMARY

Disclosed herein is a method for determining quality of semen sample. The method comprises capturing a video of live semen sample being examined, and converting the video into a plurality of image frames. Then, the method comprises identifying, by a semen quality analysis system, one or more objects in each of the plurality of image frames of the semen sample, based on predetermined image processing techniques. Further, the method comprises generating trajectory of each of the one or more objects by tracking movement of each of the one or more objects across the plurality of image frames, and by compensating drift velocity of the semen sample. Upon generating the trajectory, the method comprises classifying the trajectory of each of the one or more objects into one or more sperm object trajectories and one or more non-sperm object trajectories. Once the trajectories are generated, the method comprises computing a total concentration estimate of the semen sample based on each of the one or more sperm object trajectories and each of the one or more non-sperm trajectories. Further, the method comprises computing a total motility estimate of the semen sample based on each of the one or more sperm object trajectories. Finally, the method comprises generating a semen quality index based on the total concentration estimate and the total motility estimate, for determining quality of the semen sample.

Further, the present disclosure relates to a semen quality analysis system for determining quality of semen sample. The semen quality analysis system comprises a processor, and a memory. The memory is communicatively coupled to the processor, and stores processor-executable instructions, which on execution, cause the processor to identify one or more objects in each of plurality of image frames, which are obtained by converting a video of live semen sample being examined, based on predetermined image processing techniques. Further, the instructions cause the processor to generate trajectory of each of the one or more objects by tracking movement of each of the one or more objects across the plurality of image frames, and by compensating drift velocity of the semen sample. Upon generating the trajectory, the instructions cause the processor to classify the trajectory of each of the one or more objects into one or more sperm object trajectories and one or more non-sperm object trajectories. Once the trajectories are classified, the instructions cause the processor to compute a total concentration estimate of the semen sample based on each of the one or more sperm object trajectories and each of the one or more non-sperm trajectories. Further, the instructions cause the processor to compute a total motility estimate of the semen sample based on each of the one or more sperm object trajectories. Finally, the instructions cause the processor to generate a semen quality index based on the total concentration estimate and the total motility estimate, for determining quality of the semen sample.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and regarding the accompanying figures, in which:

Figure 1:
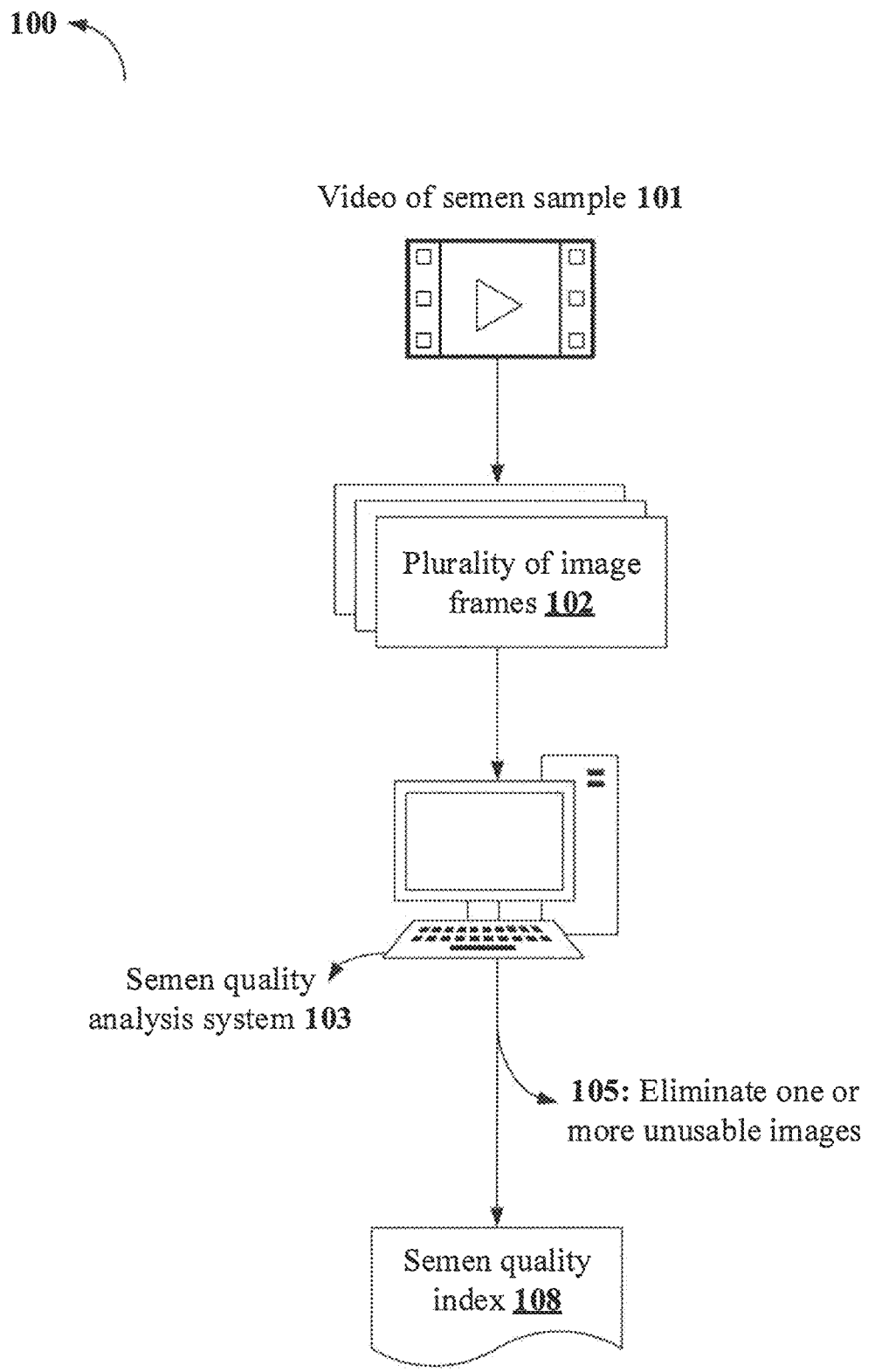
FIG. 1 illustrates an exemplary environment of determining quality of semen sample in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the specific forms disclosed, but on the contrary, the disclosure is to cover all modifications, equivalents, and alternative falling within the spirit and the scope of the disclosure.

The terms "comprises", "comprising", "includes", or any other variations thereof, are intended to cover a non-exclusive inclusion, such that a setup, device, or method that comprises a list of components or steps does not include only those components or steps but may include other components or steps not expressly listed or inherent to such setup or device or method. In other words, one or more elements in a system or apparatus preceded by "comprises . . . a" does not, without more constraints, preclude the existence of other elements or additional elements in the system or method.

The present disclosure relates to a method and a semen quality analysis system for determining quality of semen sample. The present disclosure provides an automated method for analysis of human semen quality using microscopic video sequences of the live semen sample. The video sequences may be captured through an automated microscope at a magnification, say 400×, and converted into a plurality of image frames. In each image frame, objects of interests may be identified using image processing techniques, and the identified objects of interests may be further differentiated using predetermined classification techniques, such as a multi-level convolutional neural network (CNN) technique, to classify them into sperm objects and non-sperm objects. Further, a frame-wise count of the sperm objects and the non-sperm objects may be used to estimate a total concentration estimate of the sperm objects and the non-sperm objects in a unit volume of the semen sample.

In an embodiment, individual sperm objects may be tracked across each image frames for generating a trajectory of each of the sperm objects. Based on the trajectories of each of the sperm objects, the sperm objects may be classified into progressively motile, non-progressively motile and immotile types, as per the WHO guidelines. Finally, a differential count of each type of the sperm objects may be calculated for determining a total motility estimate of the semen sample. In some instances, collisions and occlusions among the sperm objects may be effectively handled using a predictive tracking approach. As an example, there could be two major kinds of occlusions that could plague the tracking of the sperms. (i) Occlusion due to movement between the layers of the fluid. In this scenario, the sperm moves between the layers of the fluid. Essentially, the sperm appears on the surface for some period of time and then gets occluded when it goes below the surface of the fluid and eventually, it might or might not appear on the surface again. (ii) Occlusions between sperms that is when two sperms trajectories are intersecting at a common point, it becomes difficult to estimate the direction of the sperms. In addition, the present disclosure includes estimating a drift motion/velocity in the semen sample, and compensating the drift velocities, for enhancing accuracy of the motility estimation of the semen sample.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates an exemplary environment 100 of determining quality of semen sample in accordance with some embodiments of the present disclosure.

The environment 100 includes a semen quality analysis system 103 that receives a captured video of semen sample 101 (hereinafter referred to as the video 101) being examined, and converts the video 101 into plurality image frames 102 of the semen sample. In an embodiment, the video 101 of the semen sample may be captured using an image/video capturing apparatus that includes a microscope for focusing one or more objects in the semen sample, along with an image/video capturing device for capturing a focused view of the one or more objects in the semen sample. In an implementation, the image/video capturing device (not shown in FIG. 1) may be attached to an eyepiece or an ocular lens of the microscope. Further, as an example, the video 101 may be captured at a magnification of 400×, to ensure that each of the one or more objects in the semen sample are clearly visible in the plurality of image frames 102.

In an implementation, the image/video capturing apparatus, as disclosed above, may be configured within the semen quality analysis system 103. In another implementation, the image/video capturing apparatus may be configured external to the semen quality analysis system 103, and may be communicatively associated with the semen quality analysis system 103 for transferring the video 101 of the semen sample to the semen quality analysis system 103.

In an embodiment, the semen quality analysis system 103 may analyze each of the plurality of image frames 102, obtained by converting the video 101, using one or more predetermined linage processing techniques for identifying one or more unusable image frames in the plurality of image frames 102. The one or more unusable image frames may be identified and eliminated based on one or more predetermined conditions, which determine whether the plurality of image frames 102 are suitable for further processing. As an example, the one or more, predetermined conditions for determining usability of the plurality of image frames 102 may include, without limitation, density of the semen sample exceeding a predefined threshold density value, and blur level in the plurality of image frames 102 being less than a predefined blur coefficient. In an embodiment, one or more of the plurality of image frames 102 that do not satisfy the one or more predetermined conditions stated above may be considered to be unusable/unsuitable for analysis, and may be eliminated from further processing.

In an embodiment, upon assessing the usability of the plurality of image frames 102, and eliminating the one or more unusable image frames from the plurality of image frames 102, the semen quality analysis system 103 may further process the plurality of image frames 102 to identify one or more objects in the plurality of image frames 102, based on one or more predetermined image processing operations. Upon identifying the one or more objects, the semen quality analysis system 103 may generate trajectory of each of the one or more objects by tracking movement of each of the one or more objects across the plurality of image frames 102, and by compensating drift velocity of the semen sample. For example, the drift velocity/motion in the semen sample may be caused due to bending of microscope stage during analysis, or when an excess volume of the semen sample is used for analysis. Compensating the drift velocity in the semen sample may be essential to effectively determine actual velocity of each of the one or more objects from the trajectory of each of the one or more objects. Thus, compensating the drift velocity helps to prevent erroneous estimation of motility of the one or more objects, due to overestimation of the motility.

In an embodiment, upon generating the trajectory of each of the one or more objects, the semen quality analysis system 103 may classify the trajectory of each of the one or more objects into one or more sperm object trajectories and one or more non-sperm object trajectories using a predetermined classification technique, such as a multi-level Convolutional Neural Network (CNN) classifier technique on the trajectory of the one or more objects. Further, the semen quality analysis system 103 may compute a total concentration estimate 213 of the semen sample based on each of the one or more sperm object trajectories and each of the one or more non-sperm trajectories. Similarly, a total motility estimate of the semen sample may be computed based on straight-line velocity of each of the one or more sperm object trajectories. Finally, the semen quality analysis system 103 may generate a semen quality index 108 based on the total concentration estimate 213 and the total motility estimate, thus computed, for determining the quality of the semen sample.

Figure 2:
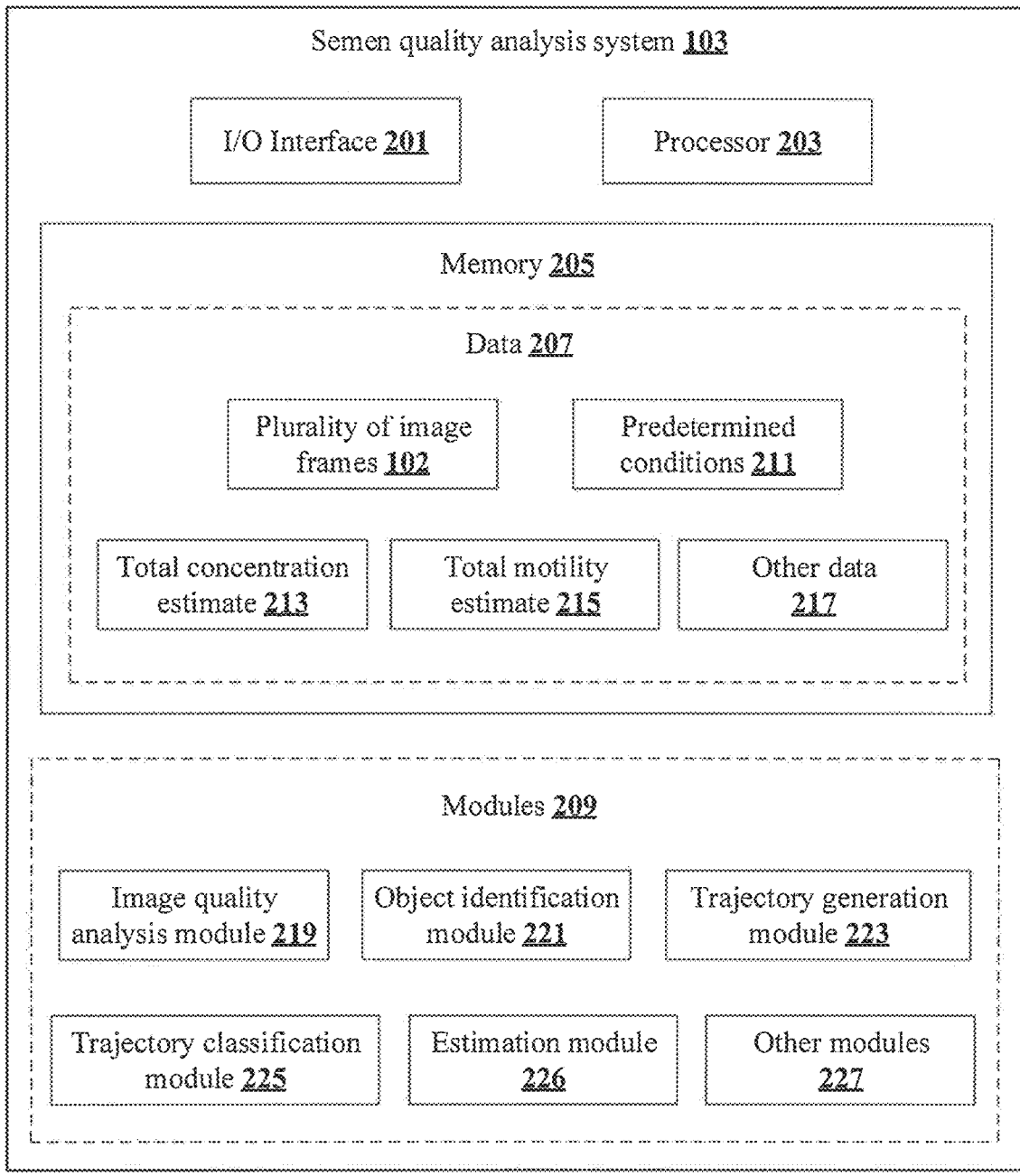
FIG. 2 shows a detailed block diagram illustrating a semen quality analysis system for determining quality of semen sample in accordance with some embodiments of the present disclosure.

FIG. 2 shows a detailed block diagram illustrating a semen quality analysis system 103 for determining quality of semen sample in accordance with some embodiments of the present disclosure.

In an embodiment, the semen quality analysis system 103 may include an I/O interface 201, a processor 203, and a memory 205, The I/O interface 201 may be configured to communicate with an image/video capturing apparatus, associated with the semen quality analysis system 103, for receiving a video 101 of the semen sample. The memory 205 may be communicatively coupled to the processor 203. The processor 203 may be configured to perform one or more functions of the semen quality analysis system 103 for determining quality of the semen sample.

In some implementations, the semen quality analysis system 103 may include data 207 and modules 209 for performing various operations in accordance with the embodiments of the present disclosure. In an embodiment, the data 207 may be stored within the memory 205 and may include, without limiting to, data related to the plurality of image frames 102, predetermined conditions 211, a total concentration estimate 213 of the semen sample (referred to as the total concentration estimate 213 hereinafter), a total motility estimate 215 of the semen sample (referred to as the total motility estimate 215 hereinafter), and other data 217.

In some embodiments, the data 207 may be stored within the memory 205 in the form of various data structures. Additionally, the data 207 may be organized using data models, such as relational or hierarchical data models. The other data 217 may store data, including temporary data and temporary files, generated by the modules 209 for determining quality of the semen sample.

In an embodiment, the plurality of image frames 102 of the semen sample are obtained by converting a captured video 101 of the semen sample. As an example, each of the plurality of image frames 102 may be at a magnification of 400×.

In an embodiment, the one or more predetermined conditions 211 are the conditions used for analyzing each of the plurality of image frames 102, and eliminating one or more unusable image frames from the plurality of image frames 102. As an example, the one or more predetermined conditions 211 for determining usability of the plurality of image frames 102 may include, without limiting to, density of the semen sample exceeding a predefined threshold density value, and blur level in the plurality of image frames 102 being less than a predefined blur coefficient.

The total concentration estimate 213 of the semen sample may indicate concentration of sperm objects in the semen sample, concentration of non-sperm objects in the semen sample, and a ratio of concentration of the sperm objects and the non-sperm objects. In an embodiment, the total concentration estimate 213 may be computed based on each of the one or more sperm object trajectories and each of the one or more non-sperm trajectories. Initially, one or more average object areas in each of the plurality of image frames 102 may be identified. Further, the identified average object areas may be scaled by ratio of sperm trajectories to total trajectories, wherein the total trajectories is computed based on the count of the one or more sperm trajectories and the one or more non-sperm trajectories. Finally, the total concentration estimate 213 may be computed as a linear function of the average object areas which are scaled.

In an embodiment, the total motility estimate 215 of the semen sample indicates concentration of sperm objects in the semen sample, concentration of non-sperm objects in the semen sample, and a ratio of concentration of the sperm objects and the non-sperm objects. The total motility estimate 215 may be computed based on velocity of each of the one or more sperm trajectories, after compensating the drift velocity from the straight-line velocity of each of the one or more sperm trajectories.

In an embodiment, the data 207 may be processed by one or more modules 209 of the semen quality analysis system 103. In one implementation, the one or more modules 209 may be stored as a part of the processor 203. In another implementation, the one or more modules 209 may be communicatively coupled to the processor 203 for performing one or more functions of the semen quality analysis system 103. The modules 209 may include, without limiting to, an image quality analysis module 219, an object identification module 221, a trajectory generation module 223, a trajectory classification module 225, estimation module 226, and other modules 227.

As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality. In an embodiment, the other modules 227 may be used to perform various miscellaneous functionalities of the sperm quality analysis system 103. It will be appreciated that such modules 209 may be represented as a single module or a combination of different modules.

In an embodiment, the image quality analysis module 219 may be responsible for analyzing and/or processing each of the plurality of image frames 102 before passing the plurality of image frames 102 for further analysis. The image quality analysis module 219 may eliminate one or more unusable image frames from the plurality of image frames 102 based on one or more predetermined conditions 211. As an example, the one or more predetermined conditions 211 may include, without limiting to, density of the semen sample exceeding a predefined threshold density value, and blur level in the plurality of image frames being less than a predefined blur coefficient. Significance of each of the one or more predetermined conditions 211 stated above, in determining usability of the plurality of image frames 102 is as illustrated in the following paragraphs:

1. Density of the Semen Sample:

Identifying and tracking the one or more objects in the semen sample may become proportionately difficult with a high sample density. According to World Health Organization (WHO) laboratory manual for examination and processing of the human semen sample, a maximum concentration of 50 million/μL, is optimal for conducting motility analysis of the semen sample. Accordingly, if the density of the semen sample is more than the specified limit, then such semen sample may be excluded from the analysis. In an embodiment, the density of the semen sample may be estimated using the following steps:
  A. Converting the image frame of the semen sample into grayscale images;
  B. Blurring the grayscale images using a Gaussian kernel;
  C. Generating an edge image using Laplacian operator;
  D. Eliminating noise, and strengthening the edges in the edge image to get a more definitive set of edges using morphological image opening (erosion, followed by dilation operation);
  E. Applying Otsu's binarization, followed by another set of morphological image opening to remove noisy pixels in the binarized image; and
  F. Counting number of non-zero pixels as an estimate of the density of the semen sample.

Initially, the density of the semen sample may be obtained with reference to a known concentration. Subsequently, the density may be calculated empirically with reference to a higher concentration limit, and a lower concentration limit. Further, if the density of the semen sample does not lie in the acceptable range, then the semen sample may be rejected.

2. Blur Level:

Generally, blurring of the video 101 or the plurality of image frames 102 may be caused by improper focus. Therefore, the captured video 101 may be analyzed to check whether the captured video 101 is acceptably sharp. In an embodiment, following operations may be performed on each of the plurality of image frames 102 to identify the blur level in the plurality of the images:
  A. Selecting three patches of size 512×512 at random, and then calculating variance of Laplacian of these patches;
  B. Choose maximum Laplacian of the three patches, thus selected;
  C. Obtaining a blur coefficient by dividing the variance by a total count of objects in the selected image frame. The blur coefficient is used for eliminating inconsistencies when the variance of Laplacian is high due to higher number of objects in the image, even though the objects are out-of-focus; and
  D. Accepting the one or more image frames 102 as not blurred, if the blur coefficient is above a predetermined threshold. Else, rejecting the video 101 sample. As an example, acceptable values of the blur coefficient may be generated by analyzing a large number of sharply focused and out-of-focus video 101 of the semen sample.

In an embodiment, the object identification module 221 may be responsible for identifying the one or more objects in each of the plurality of image frames 102, upon eliminating the one or more unusable image frames from the plurality of image frames 102. The object identification module 221 helps in extracting the objects of interest (both sperm objects and non-sperm objects) from the plurality of image frames 102.

Figure 3A:
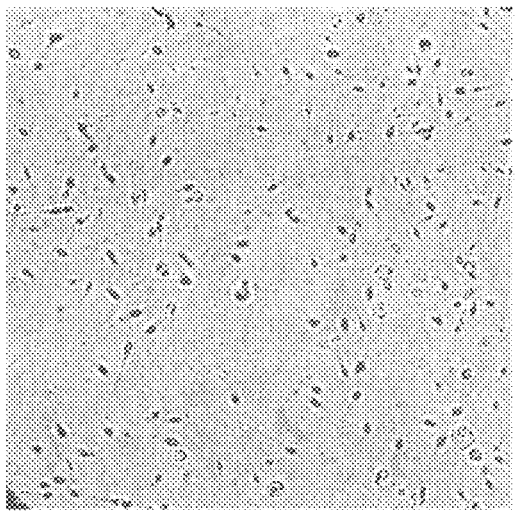
FIGS. 3A-3C are exemplary representations of an image frame while processing the image for identifying one or more objects in accordance with some embodiments of the present disclosure.
Figure 3B:
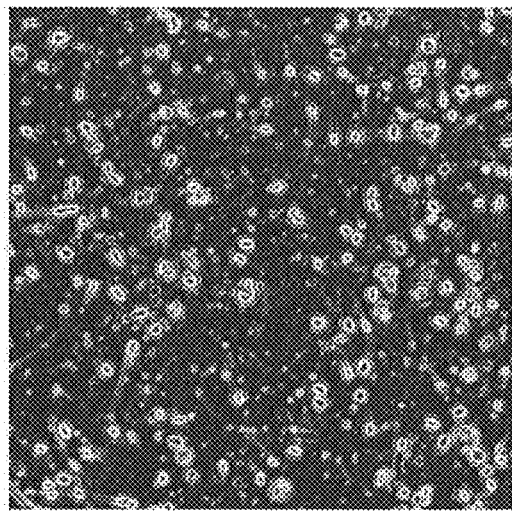
Figure 3C:
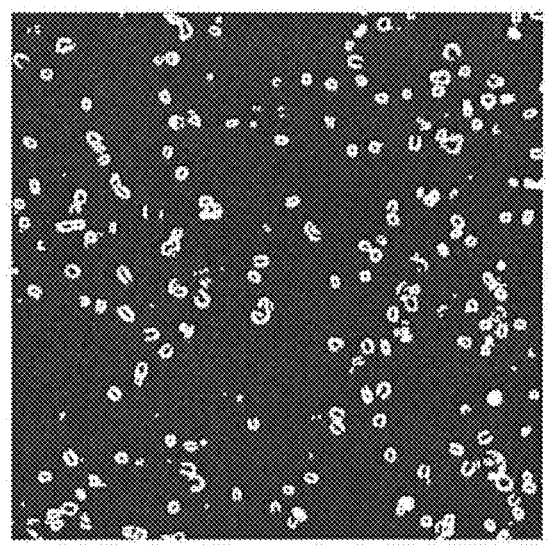

In an embodiment, a blob detection technique may be used to generate object proposals in each of the plurality of image frames 102, as illustrated in the following steps:
  A. Converting each image frame 'I' into a grayscale image '$I_g$', as shown in FIG. 3A.
  B. Applying a Gaussian blur to the image '$I_g$' with a kernel size of 11×11, to create an image '$I_b$'.
  C. Performing a Sobel edge detection on the blurred image, $I_b$ to create the Sobel image $I_s$ as shown in FIG. 3B.
  D. Performing a thresholding operation on the edge detected image $I_s$, to extract relevant blobs and contours. Here, an empirical threshold value may be selected for performing the thresholding operation. The empirical threshold value may be selected through experimentation.
  E. Perform morphological image opening to remove noisy detections as shown in FIG. 3C.

F. Applying a minimum and maximum area threshold to each blob in the noise cleaned image. These thresholds are based on the biological limits of the minimum and maximum areas of a sperm cell head. Some tolerance may be added on the higher side to account for closely placed or clumped objects, which might appear bigger. Further, only those blobs which lie within the lower and upper area thresholds are selected for further processing.

Figure 3E:
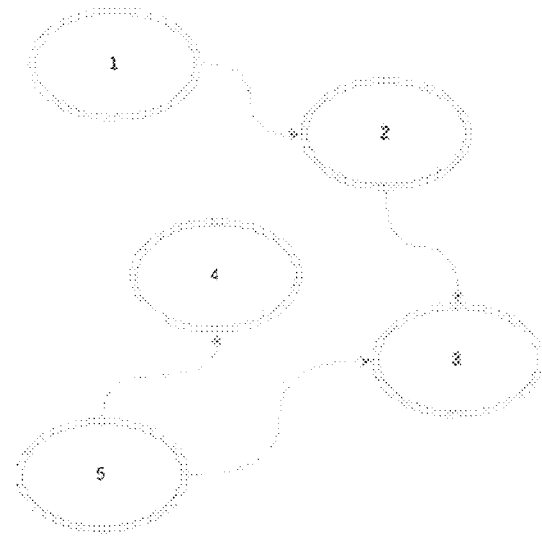
FIGS. 3E-3F show a method of associating one or more tracklets corresponding to a trajectory in accordance with some embodiments of the present disclosure.
Figure 3F:
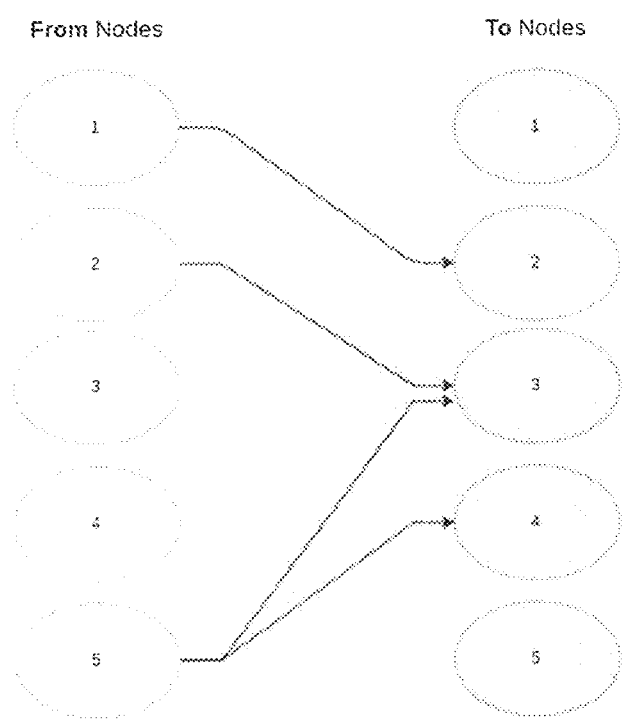
Figure 3G:
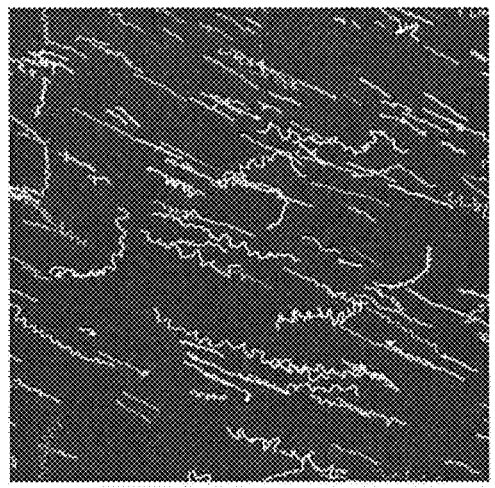
FIGS. 3G-3J show estimation of drift velocity in the semen sample in accordance with some embodiments of the present disclosure.
Figure 3G:
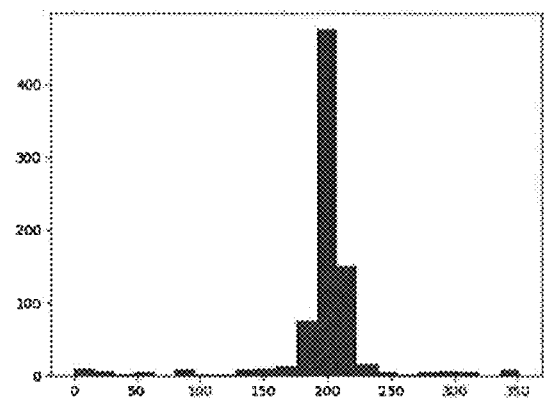
Figure 3H:
Figure 3H:
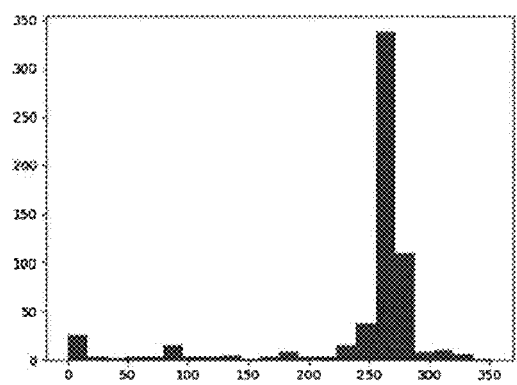
Figure 3I:
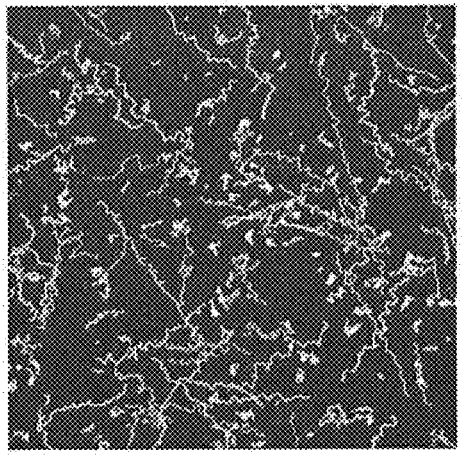
Figure 3I:
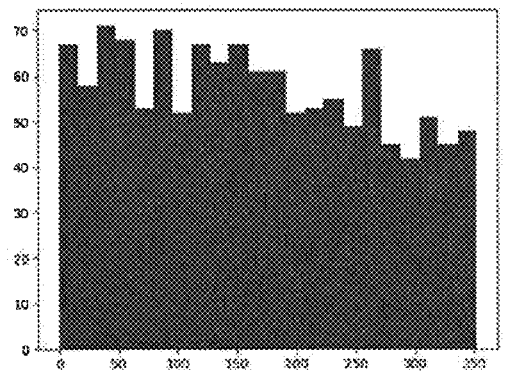
Figure 3J:
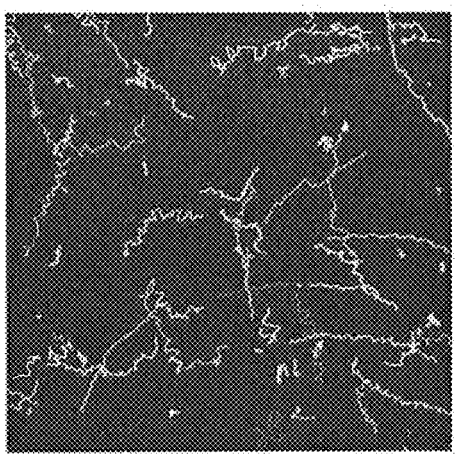
Figure 3J:
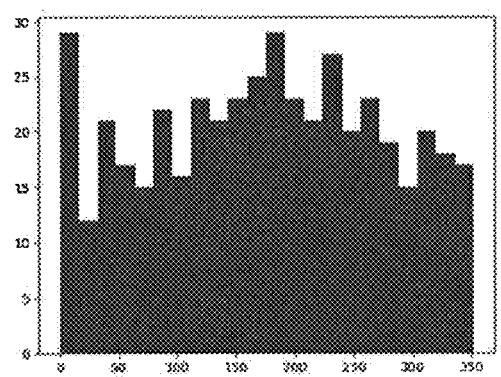
Figure 3K:
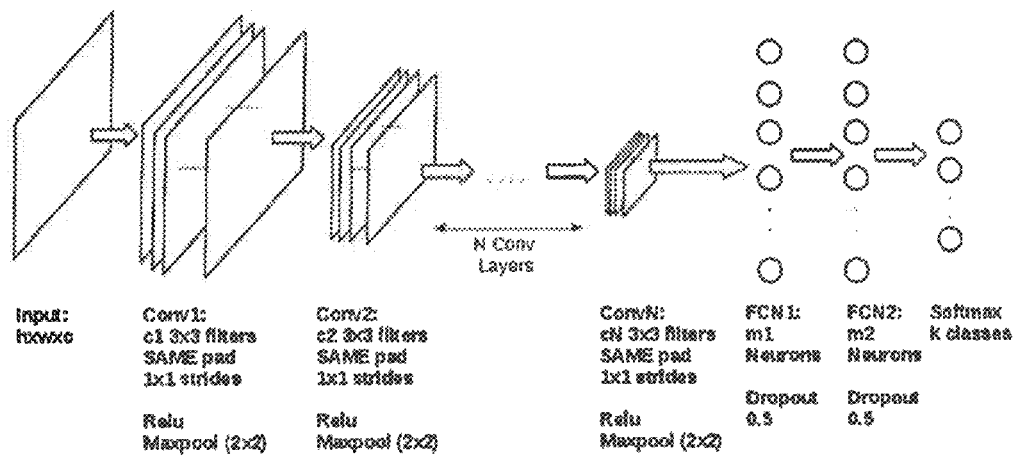
FIG. 3K illustrates a multilevel Convolutional Neural Network (CNN) architecture used for classification of one or more objects in accordance with some embodiments of the present disclosure.
Figure 3L:
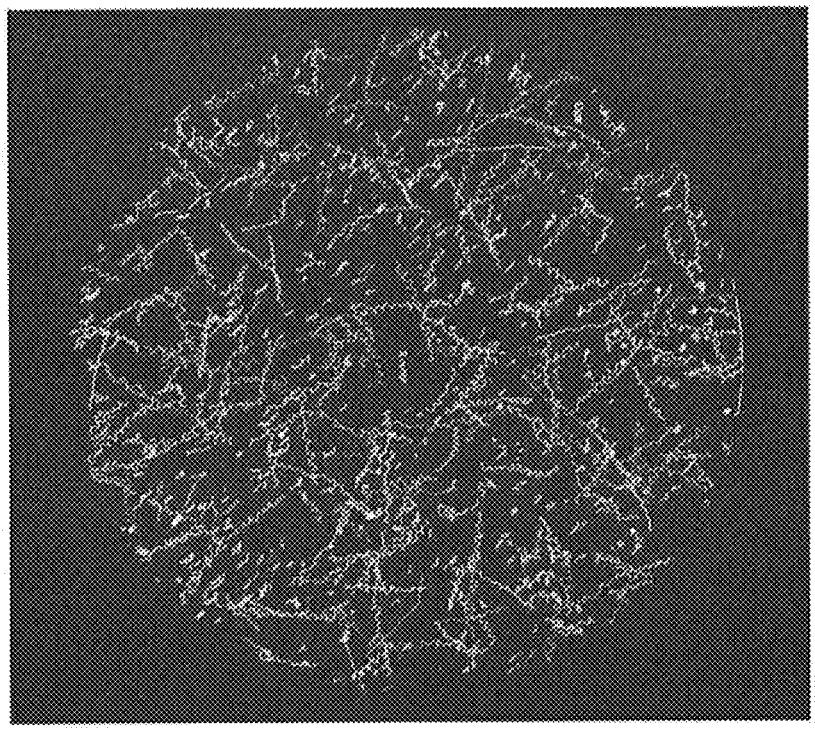
FIG. 3L is exemplary view of the one or more sperm object trajectories in the semen sample in accordance with some embodiments of the present disclosure.

In an embodiment, the trajectory generation module 223 may be responsible for generating trajectory of each of the one or more objects by tracking movement of each of the one or more objects across the plurality of image frames 102, and by compensating drift velocity of the semen sample, as shown in FIG. 3L. Each of the one or more objects may be tracked across each of the plurality of image frames 102, and one or more corresponding trajectories may be generated using a three-step process as following:

1. Generation of tracklets.
2. Association of tracklets.
3. Compensation for drift motion.

1. Generation of tracklets:

One of the issues during tracking of the one or more objects, more specifically, the sperm objects, is to form a correct association between a new sperm detection in the current frame with one of the existing tracks. The movement pattern of each of the sperm objects may be very complex, with sudden changes in direction of their movements. Further, the sperm objects may frequently move from the surface of the seminal liquid to a lower layer, which drastically changes their appearance across the plurality of image frames 102. Thus, it is difficult to create a motion model for the sperm objects. The detection responses from the extraction phase may be combined for the neighboring frames into tracklets, by using an association cost between the responses across the plurality of image frames 102.

Suppose, a tracklet may be denoted as:

$$T_i = [d_i^{t_n}] \; n = 1 \ldots N$$

Wherein,

'N' is the number of frames in the tracklet $T_i$ and $d_i^{t_n} = (X_n; Y_n)$, represents a detection response for the $i^{th}$ tracklet at a time $t_n$. This association of detections for a simile tracklet would then define the motion of a single sperm cell in the video sequence and/or across the image frames 102 from $t_1 \to t_N$. Further, the motion trajectories of the one or more objects may be generated as outlined below:

For each detection in $\{d_1^{t_i}, d_2^{t_i} \ldots d_k^{t_i}\}$, in the frame with a time-stamp $t_i$, one of the following actions may be performed:

A. Associate the detection with an existing track by solving a generalized assignment problem based on some association cost; or B. Initialize a new track tor that detection, if it cannot be associated with an existing track.

The cost of assignment for the $i^{th}$ detection at time $t_s$ to the $j^{th}$ existing track ($T_j$) may be calculated as following:

$$C_{ij}^{t_s} = \begin{cases} \|d_i^{t_s} - P_j^{t_s}\|_2, & \text{if } \|d_i^{t_s} - P_j^{t_s}\|_2 \leq 15 \; \mu M \\ \infty & \text{otherwise} \end{cases}$$

Here, $P_j^{t_s}$ is the prediction from the track $T_j$ at time $t_s$ and may be calculated as following:

$$P_j^{t_s} = \begin{bmatrix} c_x & v_x \\ c_y & v_y \end{bmatrix} * \begin{bmatrix} 1 \\ t_s \end{bmatrix}$$

Wherein, values of $v_x$, $c_x$, and $v_y$, $c_y$ may be calculated using the below calculations:

$$\begin{bmatrix} t_1 \\ t_2 \\ \vdots \\ t_{s-1} \end{bmatrix} * [v_x \; v_y] + 1 * [c_x \; c_y] = \begin{bmatrix} x_1 & y_1 \\ x_2 & y_2 \\ \vdots & \vdots \\ x_{s-1} & y_{s-1} \end{bmatrix}$$

Here, $(x_k, y_k)$; $k=1$, $s-1$ are previous detection responses assigned to a particular tracklet up to a time $t_s-1$. Further, in order to correctly associate a new object detection to one of the existing tracklets, a generalized version of linear assignment sum may be modeled as following:

$$\min \sum_{i=1}^{m} \sum_{j=1}^{n} C_{ij} x_{ij}$$

Such that, $$\sum_{i=1}^{m} x_{ij} = 1 \quad j = 1, \ldots, n$$

Where $X=[x_{ij}]$ is a Boolean matrix, where a true value represents an association between a tracker and a new detection. Here 'm' is the number of active tracklets and 'n' is the number of new detections. Further, the cost matrix $C=[C_{ij}]$ may be computed with each element representing a cost of assignment between the $i^{th}$ track and the $j^{th}$ detection in the current frame.

Further, the Hungarian algorithm may be applied to generate matches between the tracklets and the new candidate detections. However, solving the above problem using the Hungarian algorithm becomes slower with increasing number of tracklets (or detections). The linear sum assignment problem, also known as the minimum weight matching algorithm, may be used to overcome this limitation. The cost-of-assignment matrix 'C' is likely to have many infinite cost elements as there will be obvious non matches due to spatial constraints, i.e. detections too far apart from each other will have infinite cost of association. Thus, there may be many small connected components in 'C' when it is viewed as a bipartite graph. These individual connected components may be then solved independently for minimum weight matching to compute the complete tracks.

In an embodiment, for all valid assignments, the tracklets may be updated with assigned detection and time stamp. Also, new tracklets may be started for all the unassigned detections. Further, to keep track of assignments and invalidate inactive tracklets over time, a continuous invisible count may be maintained for all trajectories. This denotes the number of image frames 102 for which there were no assigned detections to the tracklet. The count may get incremented for a tracklet if it doesn't see any association in the current frame. Further, the count may be reset for the track when it gets associated with a detection. This allows discarding of tracks from active pool if they are not associated with a new detection for a long time.

2. Association of Tracklets:

In an embodiment, sperm trajectories may be broken in between if there are no detections, for a few frames. This may cause a real trajectory to be split into two or more tracklets. To counter this, tracklets obtained in the above process may be further associated with other tracklets, if they are deemed to belong to the same trajectory. A set of associated tracklets are then joined to form a single tracklet, which will represent a complete object trajectory. In order to achieve this, a graph may be created with each node representing a tracklet from the tracking stage. A directed edge in this graph may represent the likelihood of the two tracklets belonging to the same trajectory, with the 'From node' as a precursor and the 'To node' being the descendant.

Let $T_i$ and $T_j$ be tracklets from the tracking stage corresponding to the graph nodes i and j respectively. Also, let $t^s_i$ and $t^e_i$ be the start time and end time for $T_i$. If $T_i$ is a precursor (or descendant) of $T_j$, then the required condition for them to associated is $t^e_i < t^s_j$ (or $t^e_j < t^s_i$). The weight of the directed edge between the nodes i and j would then be calculated as:

$$W_{i \to j} = \begin{cases} \|d_i^{t^e} - d_j^{t^s}\|_2 & t_i^e < t_j^s \wedge t_j^s - t_i^e < 100 \text{ msecs} \\ \infty & \text{otherwise} \end{cases}$$

Where, $d^{te}_i$ and $d^{ts}_j$ are the detection responses of the tracklet i at end time and j at start time respectively. An edge-weight of infinity represents no edge or a disconnection. Further, the above tracklet-level association graph may be viewed as a bipartite matching problem as shown in FIG. 3E and FIG. 3F.

In an embodiment, after solving the assignment problem on the bipartite representation, it may be transformed hack into the directed tracklet-level association graph. Further, an individual connected components of the association graph may be determined to obtain a chain of associated tracklets, which are then joined to generate a final trajectory of the one or more objects.

In an embodiment, after association of the tracklets, following metrics may be calculated to characterize the movement of the sperm objects:

A. Curvilinear Velocity (VCL, in µm/s)—is the time-averaged velocity of a sperm head along its actual curvilinear path, as perceived in two dimensions under the microscope. This is a measure of cell vigor.

$VSL = d_{displacement}/\text{duration}$

B. Straight-line Velocity (VSL, in µm/s)—is the time-averaged velocity of a sperm head along the straight line between its first detected position and its last detected position.

$VCL = d_{actual}/\text{duration}$

C. Average Path Velocity (VAP, in µm/s)—is the time averaged velocity of sperm head along about its average path. This path is calculated by smoothing out the trajectory using the Kalman Filter algorithm.

D. Linearity (LIN)—is the linearity of a curvilinear path, calculated as VSL/VCL.

3. Compensation for Drift Motion:

Presence of a continuous drift in the semen sample may cause an erroneous report to be generated as the motility of the sperm objects will be overestimated. There are various well known causes for the drift motion. The most common cause may be bending of the microscope stage used for imaging. Presence of such drift in the semen sample may cause all the non-sperm objects and immotile sperms (which have no flagellar beat) to move at a constant speed in the direction of the drift. Since the semen sample preparation process is manual, such errors cannot be entirely ruled out under normal usage, and thus there is a need to detect and compensate for the drift motion.

In an embodiment, the drift velocity may be identified entirely from the particle/sperm trajectories in the semen sample. In a normal sample with no drift, the sperm object movements are nearly random and in all directions. In order to detect the presence of a drift motion, a velocity correlation method may be employed, and a covariance matrix for 'x' and 'y' components for normalized Straight Line Velocities (VSL) of the sperm object movement may be created as following:

$$X = \begin{bmatrix} v_x^1 & v_y^1 \\ v_x^2 & v_y^2 \\ \vdots & \vdots \\ v_x^n & v_y^n \end{bmatrix}$$

$$\sum = (X - E[X])^\top (X - E[X])$$

Here, n is the total number of tracklets. Further, an Eigenvalue decomposition of the above matrix 'X' yields 2 eigenvalues $\lambda_1$ and $\lambda_2$, and may be arranged in a descending order ($\lambda_1 > \lambda_2$). For a semen sample with no significant drift component, the ratio $\lambda_1:\lambda_2$ may be small (near to 1). However, for samples with a drift component, the ratio exhibits a large value (much greater than 1). The corresponding eigenvector may or may not correspond exactly to the drift direction, since there may be effects of other sperm object movements. But, the eigenvalue comparison may be the first step to detect the drift velocity in the semen sample. The eigenvalue comparison may be followed by the histogram method to determine the exact drift direction.

In an embodiment, to deduce the magnitude of this detected drift motion, a histogram for the orientations of all trajectories may be formed into N orientation bins. In case of drift, one of these bins may show significantly more objects than others (FIG. 3G-3J). Further, a median velocity of drift motion may be calculated by finding the median of all velocities present in the dominant orientation bin. This may be denoted as $V_{drift}$. Accordingly, FIG. 3G and FIG. 3H represent estimation of drift in semen samples with higher amount of drift velocity. Similarly, FIG. 3I and FIG. 3J indicate estimation of drift in semen samples with no drift velocity.

In an embodiment, the trajectory classification module 225 may be responsible for classifying the trajectory of each of the one or more objects into one or more sperm object trajectories and one or more non-sperm object trajectories. The one or more trajectories thus generated, may belong to both motile and immotile sperm objects. The immotile trajectories may belong to both immotile sperms or other non-sperm objects present in the semen sample. A random sample of detections from each trajectory may be passed through a classification technique, such as multi-level CNNs to classify each of the one or more trajectories.

The majority prediction for each trajectory may be taken as the class of the trajectory for the semen sample. This consideration builds resilience for the drastic appearance change of sperm objects across layers of the semen sample, across each of the plurality of image frames 102. As an example, as shown in FIG. 3K, a two-set CNN may be used in patch classification setting, such that the first CNN model identifies the sperm cell patches from a particular trajectory across multiple layers and separates them out from other non-sperm trajectories. This allows elimination of certain trajectories related to non-sperm immotile objects. Further, the second CNN model may be used to further classify other non-sperm objects into round cells (such as, WBCs and spermatogonia), and epithelial cells. In an embodiment, classification of the non-sperm objects in the semen sample may be essential, as the presence of non-sperm objects in the semen sample may be indicative of testicular damage (immature germ cells), pathology of different ducts (ciliary tufts) or inflammation of the accessory glands (leukocytes). Further, the number of non-sperm objects in the semen sample may be estimated in the same fixed wet preparations as the one used for sperm object detection. Most of the existing solutions and systems do not give any insight into the presence of non-sperm objects.

In an embodiment, identification of sperm objects may be performed using a 5 layer model having CNN layers comprising of 16, 32 and 64 3×3 filters respectively, followed by 2 fully connected layers comparison of 256 neurons each, and a two-node softmax layer for classification of output. Further, for classification of the non-sperm objects, a similar architecture may be used with 2 nodes in the softmax output layers to classify the epithelial versus round cells, as described above. Finally, the number of sperm trajectories may be calculated as follows:

$$Traj_{sperm} = \frac{\text{Number of sperm-tracjectories}}{\text{Total number of trajectories}}$$

It shall be noted that, the configuration of multi-level CNN architectures disclosed herein for identification of the sperm objects, and classification of the non-sperm objects are exemplary. Also, it shall be possible for a person skilled in the art to achieve similar classification results by varying one or more of the aforesaid configurations viz., number of layers, or number of filters being used in the multi-level CNN architectures.

In an embodiment, the estimation module 226 may be responsible for computing the total concentration estimate 213 and the total motility estimate 215 of the semen sample.

A. Total Concentration Estimation:

Initially, a total count of one or more objects in the semen sample may be calculated based on average foreground area for a FOV. Then, a fraction of the one or more object trajectories classified as sperms trajectories may be incorporated as a decay factor for the average area. Further, the linear relationship may be determined as shown below, to estimate the final concentration in Millions/μL of the semen sample.

$$Conc = \alpha*(Area_{fg}*Traj_{sperm}) + \beta$$

Where,

'Conc' is the concentration of the semen sample;

'$Area_{fg}$' is the average foreground area calculated as described above;

'$Traj_{sperm}$' is the fraction of trajectories which are classified as the sperm trajectories as described;

'α' and 'β' are the coefficients to map the average area value to concentration to the unit Millions/μL of the semen sample.

B. Total Motility Estimation:

The motility parameters may be assessed using measurement of the straight-line velocities of the one or more object trajectories. Assuming a homogeneous drift motion model for the semen sample, the calculated drift velocity, $v_{drift}$ may be subtracted from all the existing straight-line velocity vectors $V_{vsl}$. Further, the drift compensated velocities, $V^{drift}_{vsl}$ may be further used for estimation of motility parameters as following:

$$V_{vsl}^{drift} = V_{vsl} - V_{drift}$$

Finally, in order to obtain the total immotile concentration, and to account for any tiny amount of remaining drift motion, a threshold of 1 μm/s may be used. Therefore, trajectories having velocities below the threshold value may be regarded as immotile sperm objects. Further, the immotility and motility may be calculated by calculating the immotile count and motile count as a percentage of the total number of trajectories generated for the semen sample.

Figure 4:
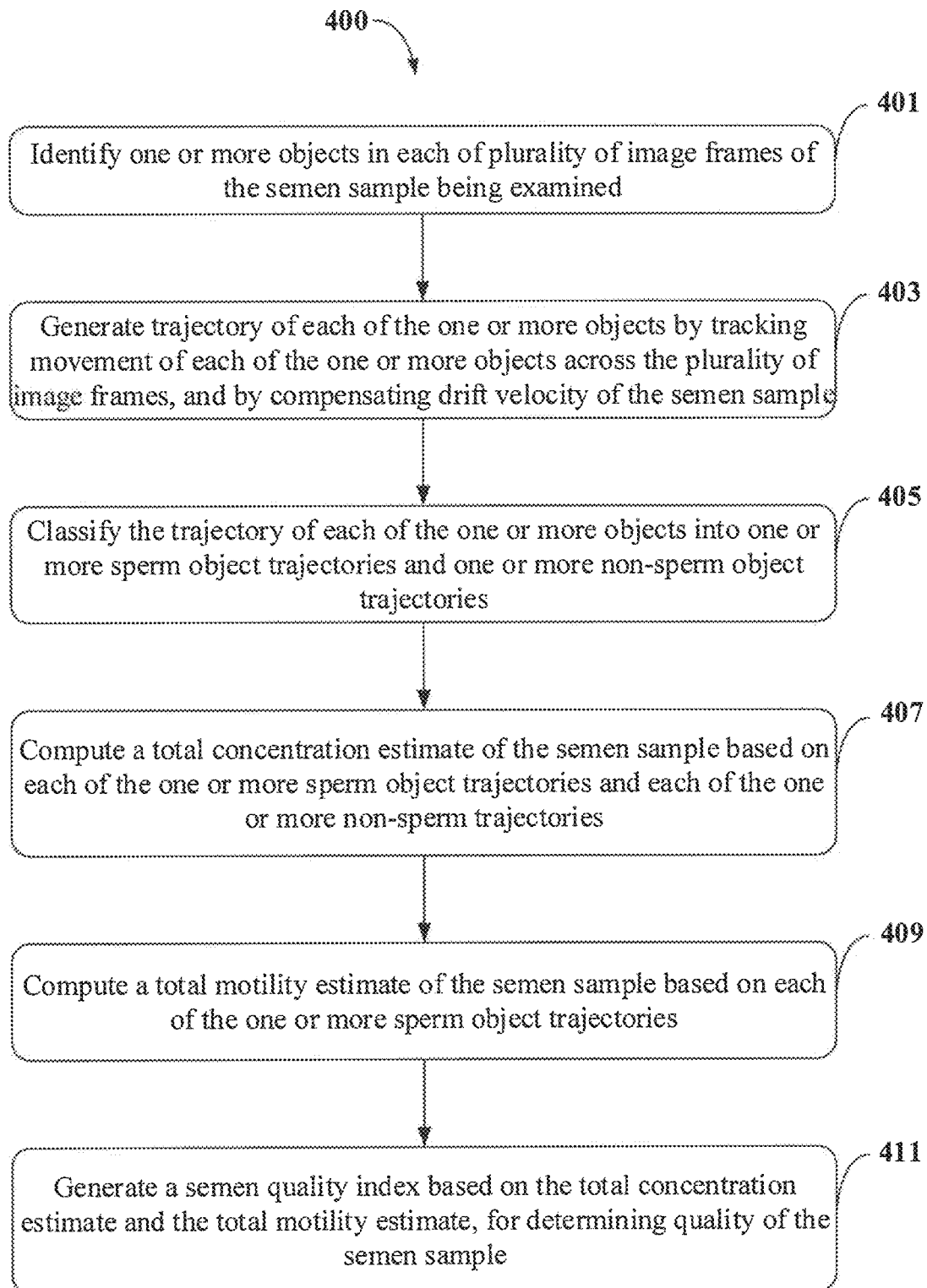
FIG. 4 shows a flowchart illustrating a method for determining quality of semen sample in accordance with some embodiments of the present disclosure.

FIG. 4 shows a flowchart illustrating a method for determining quality of semen sample in accordance with some embodiments of the present disclosure.

As illustrated in FIG. 4, the method 400 includes one or more blocks illustrating a method for determining quality of semen sample using a semen quality analysis system 103, for example the semen quality analysis system 103 of FIG. 1. The method 400 may be described in the general context of computer executable instructions. Generally, computer executable instructions can include routines, programs, objects, components, data structures, procedures, modules, and functions, which perform specific functions or implement specific abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

Initially, a video 101 of live semen sample may be captured using an image/video capturing apparatus associated with the semen quality analysis system 103. Subsequently, the captured video 101 of the semen sample may be converted into a plurality of image frames 102. Further, at block 401, the semen quality analysis system 103 may identify one or more objects in each of the plurality of image frames 102 based on predetermined image processing techniques. Further, one or more unusable image frames 102 from the plurality of image frames 102 may be eliminated based on one or more predetermined conditions 211. As an example, the one or more predetermined conditions 211 for determining usability of the plurality of image frames 102 may include, without limiting to, density of the semen sample exceeding a predefined threshold density value, and blur level in the plurality of image frames 102 being less than a predefined blur coefficient.

At block 403, the method 400 comprises generating, by the semen quality analysis system 103, trajectory of each of the one or more objects by tracking movement of each of the one or more objects across the plurality of image frames 102, and by compensating drift velocity of the semen sample. In an embodiment, the movement of each of the one or more objects may be tracked by identifying tracklets corresponding to each of the one or more objects in each of the plurality of image frames 102. Upon identifying the tracklets, displacement of the tracklets may be determined based on an initial position and a final position of the tracklets across the plurality of image frames 102. Further, a match for the tracklets, identified in one of the plurality of image frames 102, may be identified with the tracklets identified in other of the plurality of image frames 102 based on the displacement of the tracklets. Finally, the tracklets may be associated based on the match, thus identified.

The method of associating the one or more tracklets, detected across one or more of the plurality of image frames 102, may be elaborated using the following example. Suppose, the video 101 of a semen sample being examined is converted into 40 image frames 102. Now, while tracking movement of an object X across all the 40 image frames 102, a first tracklet of the object X may be continuously detected, say, between image frames 1 to 20 (out of the 40 image frames), and then the track may be lost due to various factors. Subsequently, say, a second tracklet is detected in the image frames 23 to 35. In the above scenario, an association among the first tracklet and the second tracklet may be determined, only if an end position of the first tracklet is sufficiently close to a start position of the second tracklet. On the other hand, if the final position of the first tracklet, and the start position of the second tracklet are not close, then the first tracklet and the second tracklet are considered to be unrelated.

In an embodiment, the drift velocity of the semen sample may be compensated by computing straight-line velocity of each of the one or more objects, and subtracting the drift velocity from the straight-line velocity of each of the one or more objects.

At block 405, the method 400 comprises classifying, by the semen quality analysis system 103, the trajectory of each of the one or more objects into one or more sperm object trajectories and one or more non-sperm object trajectories. In an embodiment, the trajectory of each of the one or more objects may be classified by identifying a random number of object detections from the trajectory of each of the one or more objects. Further, upon identifying the random number of object detections, count of one or more sperm trajectories and one or more non-sperm trajectories, among the random number of object detections, may be determined by analyzing each of the random number of object detections using a predetermined technique, such as multi-level Convolutional Neural Network (CNN) classifier technique. Finally, the trajectory of each of the one or more objects may be classified based on majority of the count of the one or more sperm trajectories and the one or more non-sperm trajectories.

At block 407, the method 400 comprises computing, by the semen quality analysis system 103, a total concentration estimate 213 of the semen sample based on each of the one or more sperm object trajectories, and each of the one or more non-sperm object trajectories. In an embodiment, the total concentration estimate 213 may be computed by identifying one or more average object areas in each of the plurality of image frames 102 and scaling the average object areas by ratio of sperm trajectories to total trajectories. For example, the total trajectories may be computed based on the count of the one or more sperm trajectories and the one or more non-sperm trajectories. Upon scaling the average object, the total concentration may be estimated as a linear function of the average object areas, thus scaled.

In an embodiment, the total concentration estimate 213 may indicate concentration of sperm objects in the semen sample, concentration of non-sperm objects in the semen sample, and a ratio of concentration of the sperm objects and the non-sperm objects.

At block 409, the method 400 comprises computing, by the semen quality analysis system 103, a total motility estimate 215 of the semen sample based on each of the one or more sperm object trajectories. In an embodiment, the total motility estimate 215 of the semen sample may be computed based on straight-line velocity of each of the one or more sperm trajectories, after compensating the drift velocity from the straight-line velocity of each of the one or more sperm trajectories. Further, the total motility estimate 215 of the semen sample may indicate proportion of sperm objects having progressive motility among the one or more objects, proportion of the sperm objects having non-progressive motility and proportion of immotile sperm objects.

At block 411, the method 400 comprises generating, by the semen quality analysis system 103, a semen quality index 108 based on the total concentration estimate 213 and the total motility estimate 215, for determining quality of the semen sample. In an embodiment, the method 400 also includes handling occlusions among sperm objects in the semen sample before computing the total motility estimate 215 of the semen sample.

Computer System

Figure 5:
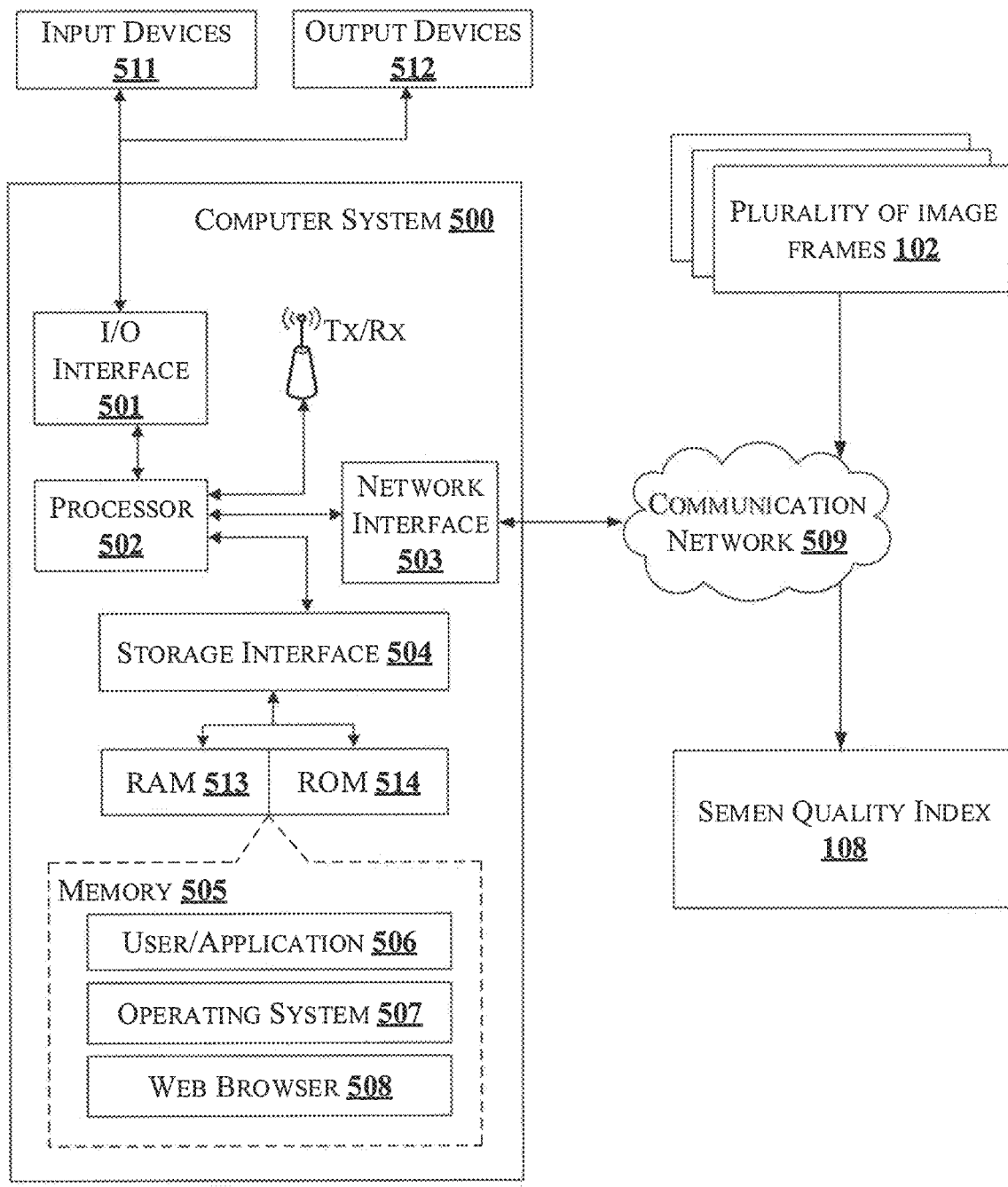
FIG. 5 illustrates a block diagram of an exemplary computer system for implementing embodiments consistent with the present disclosure.

FIG. 5 illustrates a block diagram of an exemplary computer system 500 for implementing embodiments consistent with the present disclosure. In an embodiment, the computer system 500 may be semen quality analysis system 103, which is used for determining quality of semen sample. The computer system 500 may include a central processing unit ("CPU" or "processor") 502. The processor 502 may comprise at least one data processor for executing program components for executing user- or system-generated business processes. A user may include a person, a person whose semen sample is being examined, or an animal whose semen sample is being examined. The processor 502 may include specialized processing units such as integrated system (bus) controllers, memory management control units, floating point units, graphics processing units, digital signal processing units, etc.

The processor 502 may be disposed in communication with one or more input/output (I/O) devices (511 and 512) via I/O interface 501. The 110 interface 501 may employ communication protocols/methods such as, without limitation, audio, analog, digital, stereo, IEEE-1394, serial bus, Universal Serial Bus (USB), infrared, PS/2, BNC, coaxial, component, composite, Digital Visual interface (DVI), high-definition multimedia interface (HDMI), Radio Frequency (RF) antennas, S-Video, Video Graphics Array (VGA), IEEE 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE) or the like), etc. Using the I/O interface 501, the computer system 500 may communicate with one or more I/O devices 511 and 512. In some implementations, the I/O interface 501 may be used to connect to a user device, such as a smartphone associated with the user, to notify the user about semen quality index 108, and to optionally provide one or more semen quality reports to the user.

In some embodiments, the processor 502 may be disposed in communication with a communication network 509 via a network interface 503. The network interface 503 may communicate with the communication network 509. The network interface 503 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface 503 and the communication network 509, the computer system 500 may communicate with an image/video capturing device for capturing a video of the semen sample 101. Further, the communication network 509 may be used to provide the semen quality index 108 of the semen sample, being examined, to the user.

The communication network 509 can be implemented as one of the several types of networks, such as intranet or Local Area Network (LAN) and such within the organization. The communication network 509 may either be a dedicated network or a shared network, which represents an association of several types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 509 may include a variety of network devices, including routers, bridges, servers, computing devices, storage devices, etc.

In some embodiments, the processor 502 may be disposed in communication with a memory 505 (e.g., RAM 513, ROM 514, etc. as shown in FIG. 5) via a storage interface 504. The storage interface 504 may connect to memory 505 including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 505 may store a collection of program or database components, including, without limitation, user/application 506, an operating system 507, a web browser 508, and the like. In some embodiments, computer system 500 may store user/application data 506, such as the data, variables, records, etc. as described in this invention. Such databases may be implemented as fault-tolerant, relational, scalable, secure databases such as Oracle or Sybase.

The operating system 507 may facilitate resource management and operation of the computer system 500. Examples of operating systems include, without limitation, Apple Macintosh OS X, UNIX, Unix-like system distributions (e.g., Berkeley Software Distribution (BSD), FreeBSD, Net BSD, Open BSD, etc.), Linux distributions (e.g., Red Hat, Ubuntu, K-Ubuntu, etc.), International Business Machines (IBM) OS/2, Microsoft Windows (XP, Vista/7/8, etc.), Apple iOS, Google Android, Blackberry Operating System (OS), or the like. A user interface may facilitate display, execution, interaction, manipulation, or operation of program components through textual or graphical facilities. For example, user interfaces may provide computer interaction interface elements on a display system operatively connected to the computer system 500, such as cursors, icons, check boxes, menus, windows, widgets, etc. Graphical User Interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, JavaScript, AJAX, HTML, Adobe Flash, etc.), or the like.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Advantages of the embodiment of the present disclosure are illustrated herein.

In an embodiment, the present disclosure provides a method for determining quality of a live semen sample.

In an embodiment, the present disclosure helps in generating trajectories of each objects in the semen sample, by determining tracklets of each objects across the image frames and associating the determined tracklets to form trajectories.

In an embodiment, the method of present disclosure uses a multi-level CNN classification technique on the trajectories, thereby effectively classifying the objects into sperm object trajectories and non-sperm object trajectories.

In an embodiment, the method of present disclosure computes a total concentration estimate of the semen sample using sperm object trajectories and non-sperm trajectories, thereby provides insights into overall quality of the semen sample.

In an embodiment, the method of present disclosure estimates a drift velocity/motion of the semen sample, and compensates the drift velocity from straight-line velocities of each objects while generating trajectories of the objects, thereby enhancing overall accuracy of object tracking.

In an embodiment, the present disclosure provides a completely automated method for analyzing the quality of semen sample, thereby helps in overcoming various inconsistencies, such as human errors, limitations on number of repetitions of analysis, and time required for the analysis, associated with manual analysis.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise. The enumerated listing of items does not imply that any or all the items are mutually exclusive, unless expressly specified otherwise.

The terms "a", "an" and "the" mean "one or more", unless expressly specified otherwise. A description of an embodiment with several components in communication with each other does not imply that all such components are required. On the contrary, a variety of optional components are described to illustrate the wide variety of possible embodiments of the invention.

When a single device or article is described herein, it will be clear that more than one device/article (whether they cooperate) may be used in place of a single device/article. Similarly, where more than one device or article is described herein (whether they cooperate), it will be clear that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Referral Numerals:

| Reference Number | Description |
| --- | --- |
| 100 | Environment |
| 101 | Video of semen sample |
| 102 | Plurality of image frames |
| 103 | Semen quality analysis system |
| 108 | Semen quality index |
| 201 | I/O interface |
| 203 | Processor |
| 205 | Memory |
| 207 | Data |
| 209 | Modules |
| 211 | Predetermined conditions |
| 213 | Total concentration estimate |
| 215 | Total motility estimate |
| 217 | Other data |
| 219 | Image quality analysis module |
| 221 | Object identification module |
| 223 | Trajectory generation module |
| 225 | Trajectory classification module |
| 226 | Estimation module |
| 227 | Other modules |
| 500 | Exemplary computer system |
| 501 | I/O Interface of the exemplary computer system |
| 502 | Processor of the exemplary computer system |
| 503 | Network interface |
| 504 | Storage interface |
| 505 | Memory of the exemplary computer system |
| 506 | User/Application |
| 507 | Operating system |
| 508 | Web browser |
| 509 | Communication network |
| 511 | Input devices |
| 512 | Output devices |
| 513 | RAM |
| 514 | ROM |

The invention claimed is:

1. A semen quality analysis system for determining quality of a semen sample, the semen quality analysis system comprising:
an automated microscope for capturing a video sequence of a live semen sample;
a processor; and
a memory, communicatively coupled to the processor, wherein the memory stores processor-executable instructions, which on execution, cause the processor to:
convert the video sequence to a plurality of image frames;
identify one or more objects in each of the plurality of image frames-of the semen sample being examined, based on predetermined image processing techniques;
generate a trajectory of each of the one or more objects by tracking movement of each of the one or more objects across the plurality of image frames, and by compensating drift velocity of the semen sample;
classify the trajectory of each of the one or more objects into one or more sperm object trajectories and one or more non-sperm object trajectories by:
determining a count of one or more sperm trajectories and one or more non-sperm trajectories, among random number of object detections identified from trajectory of each of the one or more objects, by analyzing each of the random number of object detections using a multi-level Convolutional Neural Network (CNN) classifier technique; and
classifying the trajectory of each of the one or more objects based on a majority of the count of the one or more sperm trajectories and the one or more non-sperm trajectories;
compute a total concentration estimate of the semen sample based on each of the one or more sperm object trajectories and each of the one or more non-sperm trajectories;
compute a total motility estimate of the semen sample based on each of the one or more sperm object trajectories; and
generate a semen quality index-based on the total concentration estimate and the total motility estimate, for determining quality of the semen sample.

2. The semen quality analysis system as claimed in claim 1, wherein the processor eliminates one or more unusable image frames from the plurality of image frames based on one or more predetermined conditions.

3. The semen quality analysis system as claimed in claim 2, wherein the one or more predetermined conditions to determine usability of the plurality of image frames-includes density of the semen sample exceeding a predefined threshold density value, and blur level in the plurality of image frames-being less than a predefined blur coefficient.

4. The semen quality analysis system as claimed in claim 1, wherein to track the movement of each of the one or more objects, the processor is configured to:
identify tracklets corresponding to each of the one or more objects in each of the plurality of image frames;
determine displacement of the tracklets based on an initial position and a final position of the tracklets across the plurality of image frames;
identify a match for the tracklets, identified in one or more of the plurality of image frames, with the tracklets, identified in other of the plurality of image frames, based on the displacement of the tracklets; and
associate the tracklets based on the match, thus identified.

5. The semen quality analysis system as claimed in claim 1, wherein to compensate the drift velocity of the semen sample, the processor is configured to:
compute a straight-line velocity of each of the one or more objects; and
subtract the drift velocity from the straight-line velocity of each of the one or more objects.

6. The semen quality analysis system as claimed in claim 1, wherein to compute the total concentration estimate, the processor is configured to:
identify one or more average object areas in each of the plurality of image frames;
scale the average object areas by ratio of sperm trajectories to total trajectories, wherein the total trajectories is computed based on the count of the one or more sperm trajectories and the one or more non-sperm trajectories; and
estimate the total concentration as a linear function of the average object areas, thus scaled.

7. The semen quality analysis system as claimed in claim 1, wherein the total concentration estimate indicates a concentration of sperm objects in the semen sample, concentration of non-sperm objects in the semen sample, and a ratio of concentration of the sperm objects and the non-sperm objects.

8. The semen quality analysis system as claimed in claim 1, wherein the total motility estimate of the semen sample is computed based on a straight-line velocity of each of the one or more sperm trajectories, after compensating the drift velocity from the straight-line velocity of each of the one or more sperm trajectories.

9. The semen quality analysis system-as claimed in claim 1, wherein the total motility estimate-of the semen sample indicates a proportion of one or more sperm objects having progressive motility among the one or more objects, a proportion of the one or more sperm objects having non-progressive motility and a proportion of the one or more sperm objects that are immotile.

10. The semen quality analysis system-as claimed in claim 1, wherein the processor is further configured to handle occlusions among one or more sperm objects in the semen sample before computing the total motility estimate of the semen sample.

11. A method for determining quality of a semen sample, the method comprising:
capturing a video sequence of a live semen sample;
converting the video sequence to a plurality of image frames;
identifying, by a semen quality analysis system, one or more objects in each of the plurality of image frames of the semen sample being examined, based on predetermined image processing techniques;
generating, by the semen quality analysis system, a trajectory of each of the one or more objects by tracking movement of each of the one or more objects across the plurality of image frames, and by compensating drift velocity of the semen sample;
classifying, by the semen quality analysis system, the trajectory of each of the one or more objects into one or more sperm object trajectories and one or more non-sperm object trajectories, the classifying comprising:
determining a count of one or more sperm trajectories and one or more non- sperm trajectories, among a random number of object detections identified from trajectory of each of the one or more objects, by analyzing each of the random number of object detections using a multi-level Convolutional Neural Network (CNN) classifier technique; and
classifying the trajectory of each of the one or more objects based on a majority of the count of the one or more sperm trajectories and the one or more non-sperm trajectories;
computing, by the semen quality analysis system, a total concentration estimate of the semen sample based on each of the one or more sperm object trajectories and each of the one or more non-sperm trajectories;
computing, by the semen quality analysis system, a total motility estimate of the semen sample based on each of the one or more sperm object trajectories; and
generating, by the semen quality analysis system, a semen quality index-based on the total concentration estimate- and the total motility estimate, for determining quality of the semen sample.

12. The method as claimed in claim 11 further comprises eliminating one or more unusable image frames from the plurality of image frames based on one or more predetermined conditions.

13. The method as claimed in claim 12, wherein the one or more predetermined conditions for determining usability of the plurality of image frames includes density of the semen sample exceeding a predefined threshold density value, and blur level in the plurality of image frames being less than a predefined blur coefficient.

14. The method as claimed in claim 11, wherein tracking the movement of each of the one or more objects comprises:
identifying tracklets corresponding to each of the one or more objects in each of the plurality of image frames;
determining displacement of the tracklets based on an initial position and a final position of the tracklets across the plurality of image frames;
identifying a match for the tracklets, identified in one or more of the plurality of image frames, with the tracklets, identified in other of the plurality of image frames, based on the displacement of the tracklets; and
associating the tracklets based on the match, thus identified.

15. The method as claimed in claim 11, wherein compensating the drift velocity of the semen sample comprises:
computing a straight-line velocity of each of the one or more objects; and
subtracting the drift velocity from the straight-line velocity of each of the one or more objects.

16. The method as claimed in claim 11, wherein computing the total concentration estimate comprises:
identifying one or more average object areas in each of the plurality of image frames; and
scaling the average object areas by ratio of sperm trajectories to total trajectories, wherein the total trajectories is computed based on the count of the one or more sperm trajectories and the one or more non-sperm trajectories; and
estimating the total concentration as a linear function of the average object areas, thus scaled.

17. The method as claimed in claim 11, wherein the total concentration estimate indicates a concentration of sperm objects in the semen sample, concentration of non-sperm objects in the semen sample, and a ratio of concentration of the sperm objects and the non-sperm objects.

18. The method as claimed in claim 11, wherein the total motility estimate of the semen sample is computed based on a straight-line velocity of each of the one or more sperm trajectories, after compensating the drift velocity from the straight-line velocity of each of the one or more sperm trajectories.

19. The method as claimed in claim 11, wherein the total motility estimate of the semen sample indicates a proportion of one or more sperm objects having progressive motility among the one or more objects, a proportion of the one or more sperm objects having nonprogressive motility and a proportion of the one or more sperm objects that are immotile.

20. The method as claimed in claim 11, further comprises handling occlusions among one or more sperm objects in the semen sample before computing the total motility estimate of the semen sample.

* * * * *